United States Patent
DeVore et al.

(12) 
(10) Patent No.: US 6,197,934 B1
(45) Date of Patent: Mar. 6, 2001

(54) COMPOUND DELIVERY USING RAPIDLY DISSOLVING COLLAGEN FILM

(75) Inventors: Dale P. DeVore, Chelmsford, MA (US); Richard A. Eiferman, Louisville, KY (US); Edwin U. Keates, Villanova, PA (US)

(73) Assignee: Collagenesis, Inc., Beverly, MA (US)

( * ) Notice: Subject to any disclaimer, the term of this patent is extended or adjusted under 35 U.S.C. 154(b) by 0 days.

(21) Appl. No.: 09/083,899

(22) Filed: May 22, 1998

(51) Int. Cl.$^7$ .......................... A61K 38/17; A61K 38/00; C07K 1/00; A61M 1/00

(52) U.S. Cl. .......................... 530/356; 530/342; 530/345; 530/402; 514/2; 514/21; 514/801; 514/912; 514/913; 604/51; 604/890.1

(58) Field of Search .................... 530/356, 342; 530/345, 402; 514/2, 21, 801, 912, 913; 604/51, 890.1

(56) References Cited

U.S. PATENT DOCUMENTS

| | | | |
|---|---|---|---|
| 4,164,559 | 8/1979 | Miyata et al. | 424/14 |
| 4,713,446 | * 12/1987 | DeVore et al. | 530/356 |
| 5,219,576 | 6/1993 | Chu et al. | 424/484 |
| 5,492,135 | 2/1996 | DeVore et al. | 530/356 |
| 5,512,301 | 4/1996 | Song et al. | 424/484 |
| 5,550,188 | 8/1996 | Rhee et al. | 525/54.1 |
| 5,631,243 | 5/1997 | Kelman et al. | 514/56 |
| 5,660,692 | 8/1997 | Nesburn et al. | 204/157.68 |

FOREIGN PATENT DOCUMENTS

| | | |
|---|---|---|
| 0 640 647 A2 | 3/1995 | (EP). |
| 0 640 647 A3 | 3/1995 | (EP). |
| 0 671 165 A2 | 9/1995 | (EP). |

OTHER PUBLICATIONS

Costa et al., *Opthalmic Surgery*, vol. 24, No. 3, pp. 152–170, 1993.*

Annen et al., "Follow Up of a Pilot Study of Trabeculectomy with Low Dosage Mitomycin C (0.2 mg/ml for 1 minute). Independent Evaluation of a Retrospective Non randomized Study," *Klin. Monatsbl Augenheilkd* 206:300–302 (1995).

Becker et al., "Comparison of Antibiotic Release from Polymethylmethacrylate Beads and Sponge Collagen," *J. Orthop Res.* 12:737–741 (1994).

Belyea et al., "Midterm Follow–Up Results of Combined Phacoemulsification, Lens Implantation, and Mitomycin–C Trabeculectomy Procedure," *J. Glaucoma* 6:90–98 (1997).

Bentz et al., "Improved Local Delivery of TGF–β2 by Binding to Injectable Fibrillar Collagen Via Difunctional Polyethylene Glycol," *J. Biomed. Mater. Res.* 39:539–548 (1998).

Bloomfield et al., "Soluble Gentamicin Ophthalmic Inserts as a Drug Delivery System," *Arch. Opthalmol* 96:885–887 (1978).

Boyce et al., "Attachment of an Aminoglycoside, Amikacin, to Implantable Collagen for Local Delivery in Wounds," *Antimicrob Agents Chemotherapy* 37:1890–1895 (1993).

Bradley et al. "Some Mechanical Property Considerations of Reconstituted Collagen for Drug Release Supports," *Biomater Med. Devices Artif. Organs* 5:159–175 (1977).

Campagna et al., "Tenon's Cyst Formation After Trabeculectomy with Mitomycin," *Ophthalmic Surg.* 26:57–60 (1995).

Cascone et al., "Blends of Synthetic and Natural Polymers as Drug Delivery Systems for Growth Hormone," *Biomaterials* 16:569–574 (1995).

Costa et al., "Wound Healing Modulation in Glaucoma Filtration Surgery," *Ophthalmic Surg.* 24:152–170 (1993).

Davidson et al., "Collagen Matrix Cisplatin Prevents Local Tumor Growth After Margin–Positive Resection," *J. Surg. Res.* 58:618–624 (1995).

Devore et al., "Delivery of Mitomycin C Using Rapidly Dissolving Collagen Films," *IOVS* 39: (1998). 1152–B33 Abstract.

Dorr et al., "In Vitro Retinoid Binding and Release from a Collagen Sponge Material in a Simulated Intravaginal Environment," *J. Biomed. Mater. Res.* 16:839–850 (1982).

Friess, "Collagen—Biomaterial for Drug Delivery," *Eur. J. Pharm. Biopharm.* 45:113–136 (1998).

Friess et al., "Insoluble Collagen Matrices for Prolonged Delivery of Proteins," *Pharm. Dev. Technol.* 1:185–193 (1996).

Gebhardt et al., "Cyclosporine in Collage Particles: Corneal Penetration and Suppression of Allograft Rejection," *J. Ocul. Pharmacol. Ther.* 11:509–517 (1995).

Gebhardt et al., "Collagen as a Delivery System for Hydrolphobic Drugs: Studies with Cyclosporine," *J. Ocul. Pharmacol. Ther.* 11:319–327 (1995).

Greenfield et al., "Late–Onset Bleb Leaks After Glaucoma Filtering Surgey," *Arch Ophthalmol* 116:443–447 (1998).

Hakim et al., "Use of Biodegradable Mesh as a Transport for a Cultured Uroepithelial Graft: An Improved Method Using Collagen Gel," *Urology* 44:139–142 (1994).

Hall et al., "Targeting Retroviral Vectors to Vascular Lesions by Genetic Engineering of the MoMLV gp70 Envelope Protein," *Hum. Gene. Ther.* 10:2183–2192 (1997).

Hasty et al., "Primate Trabeculectomies with 5–Fluorouracil Collagen Implants," *American Journal of Ophthalmology* 109:721–725 (1990).

(List continued on next page.)

Primary Examiner—Christopher S. F. Low
Assistant Examiner—Abdel A. Mohamed
(74) *Attorney, Agent, or Firm*—Clark & Elbing, LLP

(57) ABSTRACT

Disclosed herein are collagen films which rapidly dissolve at 35° C. Also disclosed are methods for the preparation of the collagen films and their use as a vehicle for delivering a dose of therapeutic compound to a specific tissue site.

7 Claims, No Drawings

OTHER PUBLICATIONS

Herschler et al., "Long–Term Results of Trabeculectomy with Collagen Sponge Implant Containing Low–Dose Antimetabolite," *Ophthalmology* 99:666–670 (1992).

Inoue et al., "Effect of a Collagen Matrix Containing Epidermal Growth Factor on Wound Contradiction," *Wound Repair Regen.* 6:213–222 (1998).

Kay et al., "Delivery of Antifibroblast Agents as Adjuncts to Filtration Surgery. Part I—Periocular Clearance of Cobalt–57 Bleomycin in Experimental Drug Delivery: Pilot Study in the Rabbit," *Ophthalmic Surg.* 17:626–630 (1986).

Kay et al., "Delivery of Antifibroblast Agents as Adjuncts to Filtration Surgry—Part II: Delivery of 5–Fluorouracil and Bleomycin in a Collagen Implant: Pilot Study in the Rabbit," *Ophthalmic Surgery* 17:796–801 (1986).

Keiji et al., "Method for Producing a Sustained Release Formulation," Chemical Abstracts 107: 183629g pp. 498 (1987).

Kitazawa et al., "Mitomycin and Trabeculectomy," *Arch Ophthalmol.* 109:1693–1698 (1991).

Kremer et al., "Adenovirus Vector–Transduced Hepatocytes Implanted via a Preformed Collagen/PTFE Support Persist for a Least 4 Weeks in vivo," *Gene Therapy* 3:932–936 (1996).

Marks et al., "Effects of Fibroblasts and Basic Fibroblast Growth Factor on Facilitation of Dermal Wound Healing by Type I Collagen Matrices," *J. Biomed. Mater. Res.* 25:683–696 (1991).

Martins et al., "The Controlled Release of Antibiotic by Hydroxyapatitie: Anionic Collagen Composites," *Artif. Organs* 22:215–221 (1998).

Matsuoka et al., "Devlopment of an Interleukin–2 Slow Delivery System," *ASAIO Trans.* 34:729–731 (1988).

Matsuoka et al., "Immunotherapy by a Slow Delivery Stem of Interleukin–2 in Mice Models," *Acta Med Okayama* 47:79–84 (1993).

McPherson, "The Utility of Collagen–Based Vehicles in Delivery of Growth Factors for Hard and soft Tissue Wound Repair," *Clin. Mater.* 9:225–234 (1992).

Megevand et al., "The Effect of Reducing the Exposure Time of Mitomycin C in Glaucoma Filtering Surgery," *Ophthalmology* 102:84–90 (1995).

Mehta et al., "Gentamicin Distribution from a Collagen Carrier," *J. Orthop Res.* 14:749–754 (1996).

Meyskens et al., "A Phase I Trial of β–All–Trans–Retinoic Acid Delivered Via a Collagen Sponge and a Cervical Cap for Mild or Moderate Intraepithelial Cervical Neoplasis," *J. Natl. Cancer Inst.* 71:921–925 (1983).

Mietz et al., "Mitomycin C for Trabeculectomy in Complicated Glaucoma: Preliminary Results After 6 Months," *Ger. J. Ophthalmol* 3:164–167 (1994).

Minabe et al., "Application of a Local Drug Delivery Sytstem to Periodontal Therapy: I. Development of Collagen Preparations With Immobilized Tetracycline," *J. Periodontal* 60:113–117 (1989).

M. S. El–Samaligy et al., "Reconstituted Collagen Nanoparticles, a Novel Drug Carrier Delivery System," *J. Pharm. Pharmacol.* 35:537–539 (1983).

Peng et al., "Cervical Tissue Uptake of All–Trans–Retinioic Acid Delivered Via a Collagen Sponge–Cervical Cap Delivery Device in Patients with Cervical Dysplasia," *Invest. New Drugs* 4:245–249 (1986).

Perka et al., "Experimental Studies of Mechanically–Induced Articular Cartilage Defects Following Implnatation of Allogeneic Embryonal Chondrocytes in a Collagen–Fibrin Gel in Chickens," *Z. Orthop. Ihre. Grenzgeb.* 134:562–572 (1996).

Puelacher et al., "Tissue–Engineered Growth of Cartilage: The Effect of Varying the Concentration of Chondrocytes Seeded Onto Synthetic Polymer Matrices," *Int. J. Oral. Maxillofac. Surg.* 23:49–53 (1994).

Punch et al., "The Release of Insoluble Antibiotics From Collagen Ocular Inserts In Vitro and Their Insertion into the Conjuctival Sac of Cattle," *J. Vet. Pharmacol. Ther.* 10:37–42 (1987).

Rao, "Recent Developments of Collagen–Based Materials for Medical Applications and Drug Delivery Systems," *J. Biomater Sci. Polym Ed.* 7:623–645 (1995).

Rao et al., "Implantable Controlled Delivery Systems for Proteins Based on Collagen—pHEMA Hydrogels," *Biomaterials* 15:383–389 (1994).

Rosenthal et al., "Collagen as Matrix for Neo–Organ Formation by Gene–Transfected Fibroblasts," *Anticancer Res.* 17:1179–1186 (1997).

Roy et al., "Extracellular Matrix Analogs as Carriers for Growth Factors; In Vitro Fibroblast Behavior," *Journal of Biomedical Meterials Research* 27:389–397 (1993).

Rubin et al., "Collagen as a Vehicle for Drug Delivery," *The Journal of Clinical Pharmacology* pp. 309–312 (1973).

Rump et al., "Mitomycin–C Concentration in Human Ocular Aqueous Humor After Topical Administration During Trabeculectomy," *Arzneimittelforschung* 45:1329–1330 (1995).

Rutten et al., "Prevention of Wound Infection in Elective Colorectal Surgery by Local Application of a Gentamicin––Containing collagen Sponge," *Eur. J. Surg. Suppl.* 578:31–35 (1997).

Shelat et al., "Results of Intraoperative 5–Fluorouracil in Patients Undergoing Trabeculectomy—Pilot Trial," *Indian J. Ophthalmol* 44:91–94 (1996).

Sielaff et al., "Characterization of the Three–Compartment Gel–Entrapment Porcine Hepatocyte Bioartificial Liver," *Cell Biol. Toxicol.* 13:357–364 (1997).

Sutton et al., "Reduction of Vinblastine Neurotoxicity in Mice Utilizing a Collagen Matrix Carrier," *Sel. Cancer Ther.* 6:35–49 (1990).

Trafney et al., "Anti–Pseudomonal Activity of Collagen Sponge with Liposomal Polymyxin B," *Pharmacol Res.* 33:63–65 (1996).

Wachol–Drewek Z et al., "Comparative Investigation of Drug Delivery of Collagen Implants Saturated in Antibiotic Solutions and a Sponge Containing Gentamicin," *Biomaterials* 17:1733–1738 (1996).

Wakitani et al., "Repair of Large Full–Thickness Articular Cartilage Defects with Allograft Articular Chondrocytes Embedded in a Collagen Gel," *Tissue Eng.* 4:429–444 (1998).

Wells et al., "Gel Matrix Vehicles for Growth Factor Application in Nerve Gap Injuries Repaired with Tubes: A Comparison of Biomatrix, Collagen, and Methylcellulose," *Experimental Neurology* 146:395–402 (1997).

Weiner et al., "Liposome–Collagen Gel Matrix: A Novel Sustained Drug Delivery," *J. Pharm. Sci.* 74:922–925 (1985).

Young et al., "Use of Mesenchymal Stem Cells in a Collagen Matrix for Achilles Tendon Repair," *J.Orthop. Res.* 16:406–413 (1998).

Chvapil, "Experimental Modifications of Collagen Synthesis and Degradation and Their Therapeutic Applications." In *Collagen in Health and Disease,* Ch. 12, pp. 206–217, Eds. J.B. Weiss and M.I.V. Jayson, Churchill Lingingston, Edinburgh, 1982.

* cited by examiner

COMPOUND DELIVERY USING RAPIDLY DISSOLVING COLLAGEN FILM

BACKGROUND OF THE INVENTION

In general, the invention relates to rapidly dissolving collagen films, methods of preparation, and the use of these films for rapid compound delivery.

The ability to specifically deliver a compound to a particular site in the human body is a desirable goal in many areas of medicine. For example, in cancer therapy, administration of chemotherapeutic agents to a tumor site with minimal exposure to surrounding tissues would dramatically reduce undesirable side effects to the surrounding tissues, or the body as a whole, while facilitating delivery of potent doses to malignant cells.

In addition, the inhibition of wound healing is beneficial in certain circumstances, for example, following glaucoma filtration surgery (otherwise known as trabeculectomy). The initial stage in the process of wound healing is characterized by the movement of intravascular components, such as plasma and blood proteins, to the extra vascular area (Peacock, In: Wound Repair, 491–492, 1984, ed. E E Peacock, WB Saunders Co, Philadelphia, Pa.). Neutrophils and macrophages then migrate to the injury site, functioning to prevent infection and promote fibroblast migration. Subsequent phases of wound healing include fibroblast secretion of collagen, collagen stabilization, angiogenesis, and wound closure (Costa et al., Opth. Surgery 24: 152–170, 1993).

During surgery for the treatment of glaucoma, a fistula is frequently created to allow for post-operative drainage of intraopthalmic fluid from the eye. Accordingly, the inhibition of fistula healing is beneficial in order to extend the drainage time and reduce intraopthalmic pressure. Several therapies have been adopted to inhibit fistula healing, including beta irradiation, 5-fluorouracil treatment, and mitomycin (also known as mitomycin-C or mitomicin) treatment (Costa et al., Opth. Surgery 24: 152–170, 1993).

SUMMARY OF THE INVENTION

The present invention provides a method of preparing a rapidly dissolving collagen film which includes a therapeutic compound. The method involves (i) preparing a purified solution of monoreactive-amine modified collagen, e.g., a glutaric anhydride derivatized collagen, (ii) heating the collagen solution to about 35–45° C. for a time sufficient to reduce collagen viscosity, (iii) adding the compound to the heated collagen solution, and iv) casting the solution into thin layers, wherein the solution dries and forms the film.

The invention also includes a collagen film prepared by the above described method and a collagen film which rapidly dissolves upon exposure to about 35° C. Preferably, the collagen film dissolves within five to ten minutes upon exposure to about 35° C. More preferably, the collagen film dissolves within two minutes upon exposure to about 35° C. Most preferably, the collagen film dissolves within one minute or 30 seconds upon exposure to about 35° C.

The therapeutic compound contained within the rapidly dissolving collagen film may be an inhibitor of cell proliferation, e.g., an anti-metabolic antibiotic, anti-metabolite, anti-fibrotic, anti-viral compound, or angiostatic compound. Preferably, the compound is an anti-metabolic antibiotic, e.g., mitomycin, daunorubicin, mithramycin, bleomycin, or doxorubicin.

Alternatively, the therapeutic compound may be an anti-metabolite. Examples of useful anti-metabolites include 5-fluorouracil, 5-fluorouridine-5'-monophosphate, 5-fluorodeoxyuridine, 5-fluorodeoxyuridine-5'-monophosphate, and 5-fluoroacetate.

In yet other applications, the therapeutic compound contained within the rapidly dissolving collagen film is an anti-fibrotic. Examples of useful anti-fibrotics include inhibitors of prolyl hydroxylase and lysyl hydroxylase, e.g., iron chelators, $\alpha,\alpha$-dipyridyl, o-phenanthroline, proline analogs, lysine analogs, and free radical inhibitors and scavengers; inhibitors of collagen secretion, e.g., colchicine, vinblastin, cytochalasin B, copper, zinc, and EGTA; inhibitors of collagen secretion and maturation, e.g., BAPN, vincristine, and D-penicillamine; and stimulators of collagen degradation, e.g., EDTA and colchicine.

As noted above, the therapeutic compound may also be an anti-viral drug. Examples of anti-viral drugs that can be used in the invention include vidarabine, acyclovir, AZT, and amantadine.

Finally, angiostatic drugs, e.g., angiostatin, as well as other miscellaneous anti-cell proliferative drugs, e.g., tissue plasminogen activator (TPA), heparin, cytosine arabinoside, and gamma-interferon, may also be used in the rapidly dissolving collagen films described herein.

In addition to methods of collagen film preparation, the invention also provides a method of rapidly delivering a compound dose to a specific tissue site in a mammal. The method involves administering a collagen film containing the compound dose to the tissue site, wherein the collagen film rapidly dissolves upon exposure to the mammalian tissue site. Using this method to deliver toxic compounds, the toxic side effects are essentially restricted to the specific tissue site of compound delivery.

In a related aspect, the invention also includes a method of treating a mammal to inhibit cellular proliferation, e.g., wound healing or tumor growth, at a specific tissue site. The method involves administering a collagen film comprising an inhibitor of cell proliferation, e.g., an anti-metabolic antibiotic, anti-metabolite, anti-fibrotic, anti-viral compound, or angiostatic compound, to the tissue site, wherein the collagen film rapidly dissolves upon exposure to the tissue and delivers a dose of the compound sufficient to inhibit cell proliferation at the tissue site.

In preferred embodiments, the cell proliferation inhibitor is mitomycin, 5-fluorouracil, or an anti-fibrotic. In addition, in other preferred embodiments, the collagen film dissolves within five to ten minutes upon exposure to the mammalian tissue site, more preferably, within two minutes, and, most preferably, within one minute or 30 seconds. In addition, the mammal is preferably a human.

This method can be used, for example, in treating a mammal undergoing surgery for glaucoma. In this application, the collagen film is administered to the trabeculectomy-created fistula in the mammal, wherein the dose of cell proliferation inhibitor is sufficient to inhibit closure of the fistula. Preferably, the cell proliferation inhibitor used is mitomycin at a dose of 200–400 $\mu$g and may be administered in a 4×4 mm collagen film patch. Most preferably, the mitomycin dose is 400 $\mu$g.

Use of this treatment results in reduced post-operative intraocular pressure. Preferably, post-operative intraocular pressure as a result of this method is less than 16 mmHg, more preferably, less than 12 mmHg, and, most preferably, less than 6 mmHg.

As used herein, by "mono-reactive amine-modified" is meant reacted with a mono-reactive amine-modifying agent, also known as a monoacylating or sulfonating agent. Useful agents include, without limitation, anhydrides, acid halides, sulfonyl halides, and active esters. The modifying agent is preferably a compound or combination of compounds which contains an acidic, carboxylic, or sulfonide group, or generates an acidic, carboxylic, or sulfonic group during reaction.

By "inhibitor of cell proliferation" is meant an inhibitor of an increase in the number of cells located at a particular site. Such inhibition may occur by inhibition of cell migration or attachment, cell replication, cell survival, or angiogenesis.

By "specific tissue site" is meant the area of tissue directly in contact with the collagen film administered to the tissue.

By "rapidly dissolves" is meant dissolves, or melts, in approximately 30 minutes or less.

The present invention provides a number of advantages. For example, the present techniques and collagen film compositions facilitate an improved approach for delivering a compound in situations where both a precise dose and accurate placement are required. The dose can be adjusted to any desired amount, i.e., by modifying the concentration of compound in the film or the size of the film, and the solid nature of the film allows its placement at any site in the body which can be reached by surgical techniques. In addition, the invention provides for the rapid dissolution of the collagen film upon exposure to normal body temperature. Taken together, these features ensure that a delivered compound achieves a certain concentration at a specific site, reducing possible inaccuracy due to mistaken dose or improper placement.

For delivery of mitomycin or 5-fluorouracil to a posttrabeculectomy fistula, the present invention represents an improvement over current empirical techniques employed, which typically involve placing a sponge wetted with compound on the fistula site for 3–5 minutes.

The advantage of delivering essentially all compound to a specific site also provides for limited compound delivery to tissues surrounding the delivery site. This advantage is especially relevant when the compound to be delivered has toxic effects. By restricting delivery to the targeted tissues, any unintentional or unnecessary toxic damage to surrounding tissues is reduced.

Furthermore, compounds, such as mitomycin, exhibit increased stability in the collagen film as compared to stability in solution. Thus, one collagen film sample preparation can be subdivided and used for several applications over the course of several weeks. This feature provides the advantages of reducing experimental variation when administered over several days and eliminating the need for daily pre-surgical sample preparation.

Other features and advantages of the invention will be apparent from the following detailed description thereof, and from the claims.

DETAILED DESCRIPTION OF THE INVENTION

Described herein are methods of preparing collagen films containing therapeutic compounds that readily dissolve upon exposure to normal human body temperature (35–37° C.). These collagen films can be used for the rapid and accurate delivery of compounds to specific tissue sites.

For the purposes of this invention, collagen can be collected, solubilized, subjected to modification by mono-reactive, amine-modifying agents, and re-precipitated by any standard technique, e.g., those provided in DeVore et al. (U.S. Pat. No. 4,713,446), herein incorporated by reference.

The following example is provided as an illustration and is in no way intended to limit the scope of the invention.

Preparation of Collagen

As a first step toward producing rapidly dissolving films, soluble collagen was prepared by standard procedures. Young calf hide was washed thoroughly with reagent alcohol and with deionized, pyrogen-free water, cut into approximately 1 $cm^2$ sections, and stirred overnight in 40 volumes of 0.5 M acetic acid. The mixture was then supplemented with pepsin (3% hide wet weight) and stirred for 72 hours. The digested, solubilized collagen was filtered through cheesecloth and precipitated by increasing the NaCl concentration to 0.8 M. The collagen was then cycled twice through steps of redissolution, in 0.5 M acetic acid, and reprecipitated. The collagen precipitate was then redissolved in 0.1 N acetic acid, dialyzed against 0.1 M acetic acid, filtered (0.45 $\mu$m), and refiltered (0.22 $\mu$m).

The purified, telopeptide-poor collagen was derivatized with glutaric anhydride as previously described (U.S. Pat. Nos. 5,631,243 and 5,492,135). Briefly, the collagen solution (approximately 3 mg/ml) was adjusted to pH 9.0 with 10 N and 1 N NaOH. While stirring the solution, glutaric anhydride was added at 10% (weight of collagen). For twenty minutes, the stirring continued, and the pH was maintained.

The pH of the solution was adjusted to 4.3 with 6 N and 1 N HCl to precipitate the derivatized collagen. The precipitate was centrifuged at 3500 rpm for 30 minutes. The pellet was washed three times in pyrogen-free deionized water and then redissolved in phosphate buffered glycerol (2% glycerol in 0.004 M phosphate buffer, pH 7.4) to achieve a final concentration of approximately 10 mg/ml.

Preparation of Collagen Films Containing Mitomycin

To prepare collagen films containing mitomycin, the collagen solution, described above, was heated in a 35° C. water bath for 30 minutes to reduce viscosity. Mitomycin (e.g., Mutamycin®, Bristol Myers Squibb, Princeton, N.J.), also known as mitomicin C, was added to the heated collagen. The collagen solution was then poured into petri dishes in a thin layer and allowed to air dry under a laminar-flow hood.

Collagen film melting time at 35° C. was measured after placing the films in 0.8% saline in a 35° C. water bath. Pre-heated collagen films melted in approximately one minute. In contrast, collagen films poured into petri dishes without pre-heating melted at 35° C. in approximately 30 minutes.

Mitomycin-containing collagen films had a final mitomycin concentration of 400 $\mu$g per 16 $mm^2$. 6 mm diameter discs were cut from the film and applied to human subconjunctival fibroblasts derived from Tenon's membrane layered in 96 well plates (CSM supplemented with 10% fetal bovine serum). After 72 hours, mitomycin-induced inhibition of cell division was assessed by measuring the reduction in fluorescence intensity (RFU) using a fluorogenic CalceinAM assay (see, for example, Decherchi et al., J. Neurosci. Meth. 71: 205 (1997); Sugita, Pflitgers Arch. 429: 555 (1995); Padanilam et al., Ann. NY Acad. Sci. 720: 111 (1994); Lichtenfels et al., J. Immunol. Meth. 172: 227 (1994); and Wang et al., Human Immunol. 37: 264 (1993)). The mitomycin-containing collagen films inhibited approximately 91% of the cell division demonstrated in control cells.

Mitomycin-containing films may be stored for later use. For example, mitomycin activity in the collagen films described above was maintained for at least 6 weeks after preparation of the films (stored at 4° C.). Administration of mitomycin-collagen films, 2, 4, and 6 weeks old, demonstrated 91%, 90%, and 92% inhibition of cell division, respectively, compared to mitomycin-free controls. These values were comparable to the % cell death inhibition elicited by administration of a freshly prepared mitomycin solution (0.4 mg/ml solution, dissolved in USP sterile water).

In contrast to the stability of mitomycin in the collagen film, HPLC analysis of the mitomycin solution determined that stability was maintained for only 4 days following storage at ambient temperature and 4° C. in the dark. Dissolution and storage in 0.9% saline or phosphate buffer (pH 7.4) is not recommended due to degradation and precipitation.

Use

Rapidly dissolving collagen films containing therapeutic compounds are useful for various treatments. For example, the collagen-mitomycin film may be administered to the external opening of the fistula created during glaucoma filtering surgery (trabeculectomy). Immediately following surgery, a collagen film, e.g., a 4×4 mm patch, containing 100–1000 μg mitomycin (preferably 400 μg), is directly applied to the external opening of the fistula prior to replacing the scleral flap. Administration of the mitomycin increases the duration of fistula patency, increasing filtration from the eye and reducing intraocular pressure.

Other compounds may also be administered to the trabeculectomy-created fistula to increase filtration during recovery. For example, 5-fluorouracil-containing films may be administered in the same fashion to deliver a 5-fluorouracil dose of 25–250 μg (preferably 100 μg). Other alternative compounds that are effective for this treatment are anti-fibrotic, angiostatic, and anti-viral compounds.

Administration of the rapidly dissolving collagen films containing inhibitors of cell proliferation are also useful for treatment during recovery from other surgical procedures where prevention of wound healing is beneficial.

In addition, the collagen films of the invention may be administered to reduce cellular proliferation in specific tissue sites, such as for the localized inhibition of neoplastic or non-neoplastic cell growth. For this application, any chemotherapeutic compound may be dissolved in the collagen matrix in concentrations appropriate for inhibiting cell growth.

OTHER EMBODIMENTS

While the treatment regimens described herein are preferably applied to human patients, they also find use in the treatment of other animals, such as domestic pets or livestock.

Moreover, while the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of rapidly delivering a compound dose to a specific tissue site in a mammal, said method comprising administering to said tissue site a rapidly dissolving collagen film, the collagen preheated in solution to at least 35° C. prior to said administering, wherein said collagen film includes said compound dose and rapidly dissolves within 30 minutes upon exposure to 35° C.

2. The method of claim 1, wherein said compound is toxic and the toxic effects of said compound are essentially restricted to said specific tissue site.

3. The method of claim 1, wherein said collagen film dissolves within ten minutes.

4. The method of claim 1, wherein said collagen film dissolves within five minutes.

5. The method of claim 1, wherein said collagen film dissolves within two minutes.

6. The method of claim 1, wherein said collagen film dissolves within one minute.

7. The method of claim 1, wherein said collagen film dissolves within thirty seconds.

* * * * *